(12) United States Patent
Andriacchi et al.

(10) Patent No.: US 8,387,277 B2
(45) Date of Patent: Mar. 5, 2013

(54) THERAPEUTIC SYSTEM AND METHOD FOR ALTERING THE GAIT OF A PATIENT

(75) Inventors: Thomas Andriacchi, Los Altos Hills, CA (US); David Scott Fisher, Terre Haute, IN (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 1102 days.

(21) Appl. No.: 12/144,569

(22) Filed: Jun. 23, 2008

(65) Prior Publication Data

US 2009/0313858 A1 Dec. 24, 2009

(51) Int. Cl.
*A61F 5/14* (2006.01)

(52) U.S. Cl. .......................................... 36/25 R; 36/142

(58) Field of Classification Search .................... 36/140, 36/142–144, 31, 88, 25 R
See application file for complete search history.

(56) References Cited

U.S. PATENT DOCUMENTS

| | | | | |
|---|---|---|---|---|
| 2,616,190 A | | 11/1952 | Darby | |
| 3,594,929 A | * | 7/1971 | Stohr | 36/44 |
| 3,738,373 A | * | 6/1973 | Glancy | 36/144 |
| 4,180,924 A | | 1/1980 | Subotnick | |
| 4,364,189 A | * | 12/1982 | Bates | 36/31 |
| 4,506,462 A | * | 3/1985 | Cavanagh | 36/92 |
| 4,547,979 A | | 10/1985 | Harada | |
| 4,620,376 A | * | 11/1986 | Talarico, II | 36/103 |
| 4,642,911 A | * | 2/1987 | Talarico, II | 36/30 R |
| 4,685,227 A | * | 8/1987 | Simmons | 36/127 |
| 4,754,561 A | * | 7/1988 | Dufour | 36/127 |
| 4,854,057 A | * | 8/1989 | Misevich et al. | 36/114 |
| 4,864,739 A | * | 9/1989 | Maestri | 36/43 |
| 5,224,810 A | * | 7/1993 | Pitkin | 36/30 R |
| 5,572,805 A | * | 11/1996 | Giese et al. | 36/30 R |
| 5,727,335 A | | 3/1998 | Kousaka | |
| 5,881,478 A | * | 3/1999 | McMahon et al. | 36/144 |
| 5,964,046 A | * | 10/1999 | Brooks | 36/28 |
| 6,349,487 B1 | * | 2/2002 | Hice | 36/140 |
| 6,604,301 B1 | * | 8/2003 | Manoli et al. | 36/43 |
| 6,725,578 B2 | * | 4/2004 | Kerrigan | 36/144 |
| 6,763,616 B2 | * | 7/2004 | Ellis, III | 36/102 |
| 6,948,262 B2 | | 9/2005 | Kerrigan | |
| 7,191,552 B1 | * | 3/2007 | Husom | 36/144 |
| 7,421,805 B2 | * | 9/2008 | Geer | 36/25 R |
| 7,464,428 B2 | * | 12/2008 | Norton | 12/146 B |
| 7,712,231 B2 | * | 5/2010 | Umezawa et al. | 36/142 |
| 7,941,941 B2 | * | 5/2011 | Hazenberg et al. | 36/28 |
| 2003/0033733 A1 | * | 2/2003 | Brooks | 36/31 |
| 2004/0040183 A1 | * | 3/2004 | Kerrigan | 36/144 |

* cited by examiner

*Primary Examiner* — Marie Patterson

(74) *Attorney, Agent, or Firm* — Vista IP Law Group, LLP

(57) ABSTRACT

The therapeutic system of the preferred embodiments includes a foot platform having a lateral segment and a medial segment. The foot platform is coupled to the foot of the patient and supports the body force of the patient. The foot platform functions to move the foot from an equilibrium position to an activated position. The transition of the foot between equilibrium position and activated position, preferably occurs substantially instantaneously once the foot platform supports greater than substantially half of the body force.

22 Claims, 4 Drawing Sheets

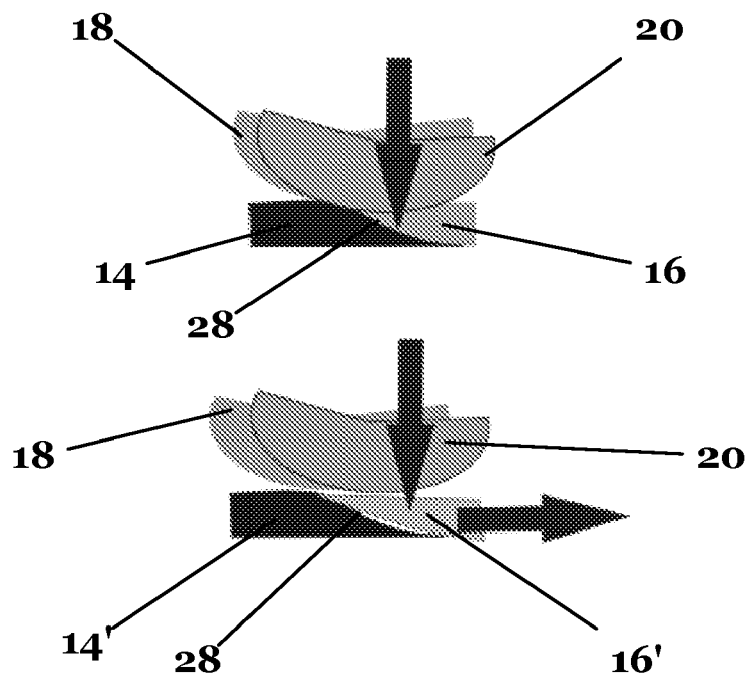
FIGURE 4.
FIGURE 5.
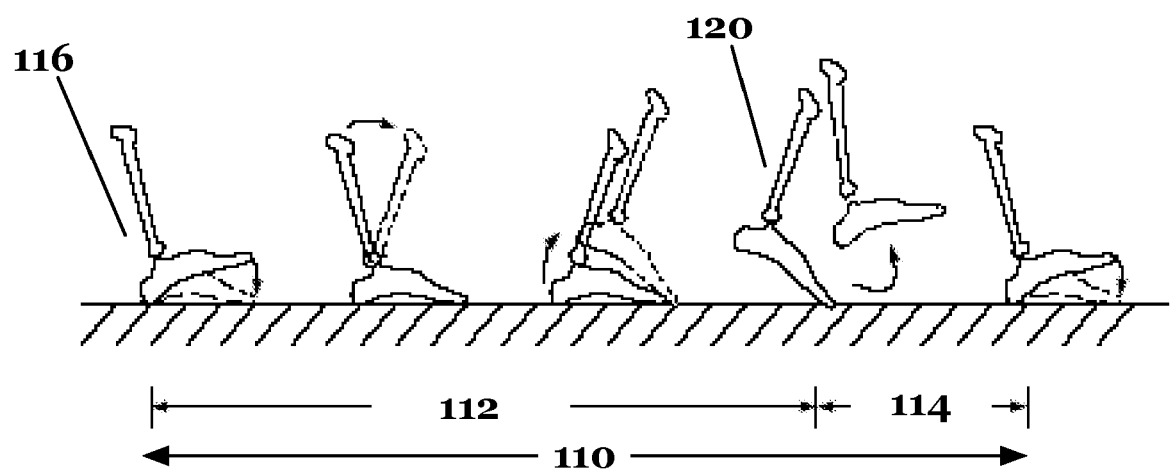
FIGURE 6.*

THERAPEUTIC SYSTEM AND METHOD FOR ALTERING THE GAIT OF A PATIENT

STATEMENT REGARDING FEDERALLY SPONSORED RESEARCH OR DEVELOPMENT

This invention was supported in part by grant number AR049792 from National Institute of Health (NIH) and Department of Veterans Affairs grant number A3476R The U.S. Government has certain rights in the invention.

TECHNICAL FIELD

This invention relates generally to the footwear field, and more specifically to an improved therapeutic system and method for altering the gait of a patient in the footwear field.

BACKGROUND

A large knee adduction moment, indicating a shift in the load from the lateral to the medial compartment, has been associated with a more rapid progression of medial compartment osteoarthritis. By reducing the peak knee adduction moment, the risk of developing knee pain and the rate of progression of medial compartment knee osteoarthritis may be slowed. Conventional shoe wedges with an increased lateral side thickness have been used to lower the peak knee adduction torque. Shoe wedges for the purposes of reducing knee adduction torque have several shortcomings, such as (i) the angle change due to wedges is always present, which causes people to adapt to a gait pattern, which will potentially reduce the effectiveness of the shoe wedge and (ii) shoe wedges can be uncomfortable, which can lead to discontinued use. Thus is a need in the footwear field to create a new and useful therapeutic system. This invention provides such a new and useful therapeutic system.

BRIEF DESCRIPTION OF THE FIGURES

FIGS. 3A, 3B, 4, and 5 are drawings of variations of the foot platform of the system.

FIG. 6 is a drawing of a gait cycle.

DESCRIPTION OF THE PREFERRED EMBODIMENTS

The following description of preferred embodiments of the invention is not intended to limit the invention to these embodiments, but rather to enable any person skilled in the art to make and use this invention.

Figure 1:
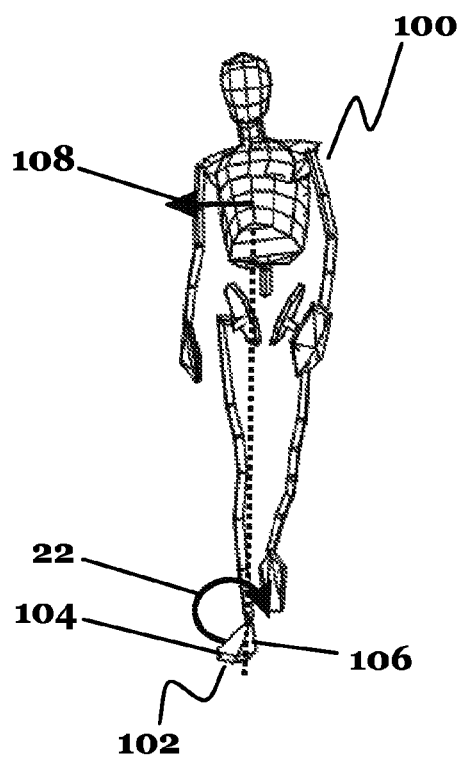
FIG. 1 is a drawing of a patient with a foot having a lateral side and a medial side.
Figure 2:
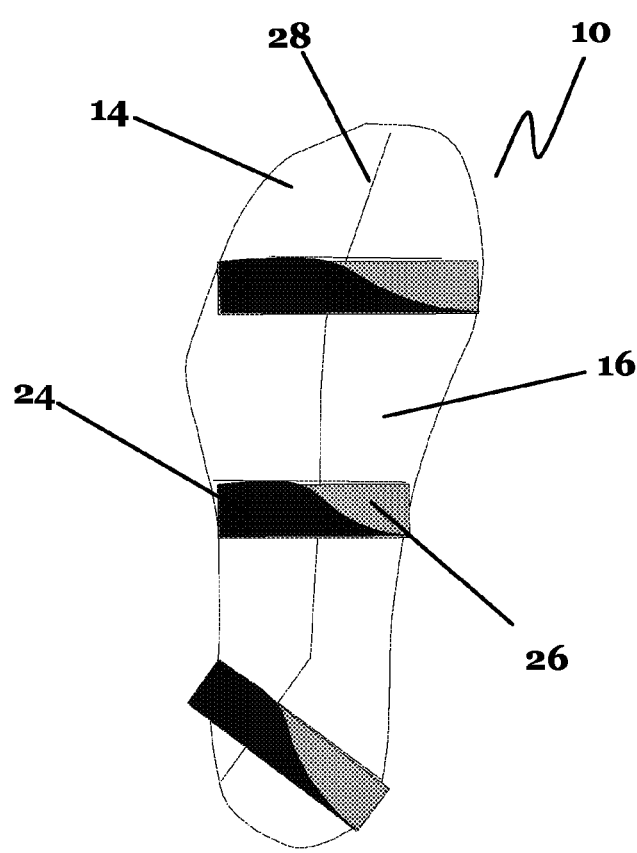
FIG. 2 is a drawing of the system of the first preferred embodiment of the invention.
Figure 3A:
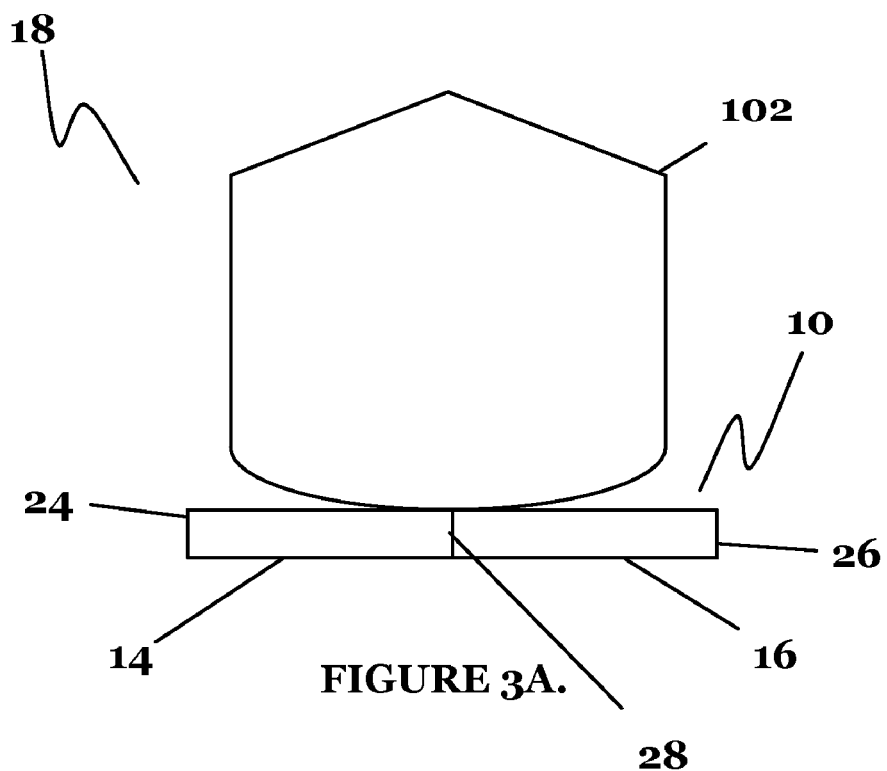
Figure 3B:
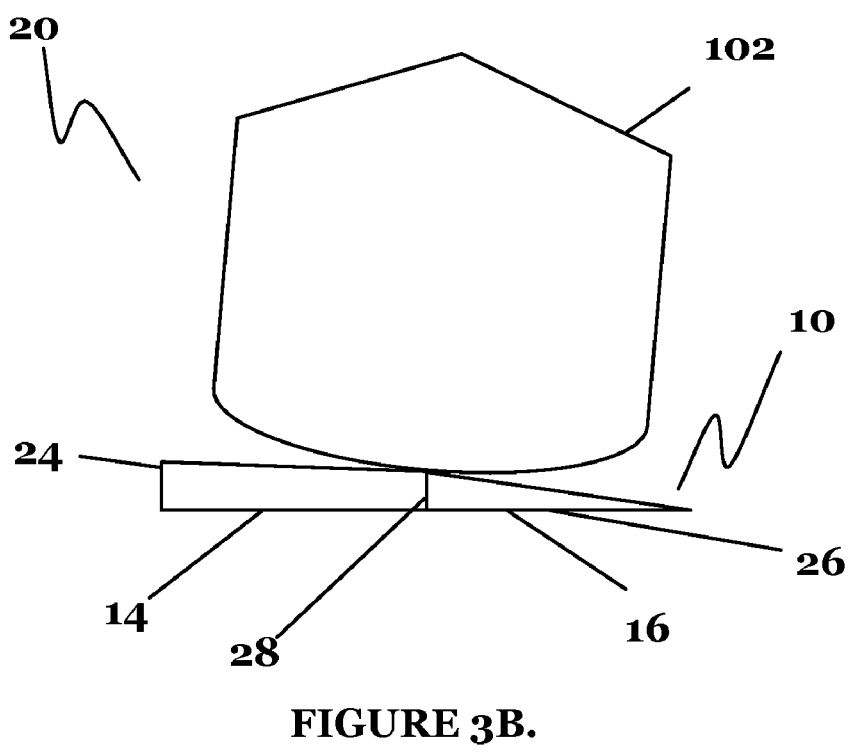

As shown in FIGS. 1 and 2, the therapeutic system of the preferred embodiments includes a foot platform 10 having a lateral segment 14 and a medial segment 16. The foot platform 10 is coupled to the foot 102 of the patient and supports the body force of the patient 100. The foot platform 10 functions to move the foot 102 from an equilibrium position 18 to an activated position 20 (as shown in FIGS. 3A and 3B). The transition of the foot 102 (as shown by arrow 22 in FIG. 1) between equilibrium position 18 and activated position 20 preferably occurs substantially instantaneously once the foot platform 10 supports greater than half of the body force. The therapeutic system and method of the preferred embodiments is preferably designed for altering the gait of the patient 100. The therapeutic system and method, however, may be alternatively used in any suitable environment and for any suitable reason.

1. Background Regarding the Patient and their Gait Cycle

As shown in FIG. 1, the therapeutic system and method of the preferred embodiments is preferably designed for a patient 100 having a body force, a foot 102 having a lateral side 104 and a medial side 106, and a knee having a medial compartment and a lateral compartment. The body force of the patient 100 induces a load in the knee that is distributed between the medial compartment of the knee and the lateral compartment of the knee.

Figure 7A:
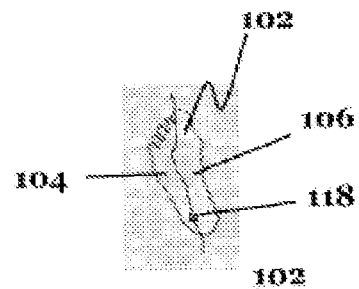
FIGS. 7A and 7B are drawings of a foot of a patient illustrating the pathway of the resultant force.
Figure 7B:
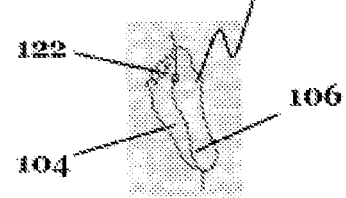

The body force of the patient 100 is preferably defined as the product of the patient's body mass and acceleration acting on the patient's body mass. When the patient 100 is in standing position, the only acceleration acting on the body mass is a gravitational acceleration and therefore, the body force is equal to the patient's weight (patient's body mass×gravitational acceleration). However, if the subject is walking, there is an additional acceleration due to the movement acting on the patient's body mass. Thus, during movement, the body force can be greater than the weight of the patient. In addition, this acceleration due the subject's movement causes the pathway of the resultant force to move in a medial-lateral direction as illustrated in FIGS. 7A and 7B.

As shown in FIG. 6, the therapeutic system and method of the preferred embodiments is designed for a patient having a gait cycle 110. The gait cycle 110 preferably includes a walking gait cycle, a running gait cycle, and any other suitable gait cycle. In addition to the gait cycle 110, the therapeutic system and method of the preferred embodiments is designed for a patient that also has a standing position. In standing position, the foot 102 is supporting approximately half of the body force because the body force of the patient 100 is distributed substantially evenly across the two feet of the patient 100.

A complete gait cycle 110 of the patient begins with a heel strike 116 of one foot 102 and ends at the next heel strike of the same foot 102. The gait cycle 110 includes a stance phase 112 and a swing phase 114. The stance phase 112 begins with a heel strike 116 in which the patient places their foot 102 (heel first) on the ground surface 124, as shown in FIG. 6, and ends with a toe off 120 in which the patient lifts the same foot 102 from the ground surface 124. During at least a portion of the stance phase 112, the foot 102 supports greater than half of the body force. During at least a portion of the stance phase 112, only one of the two feet of the patient 100 (foot 102) is in contact with the ground surface and therefore, foot 102 is supporting the majority, if not all, of the body force of the patient 100 and can exceed the weight of the subject due to the acceleration acting on the body during movement. When the patient 100 performs a heel strike 116 in the stance phase 114, the body force of the patient 100 has a heel strike location of resultant force 118, as shown in FIG. 7A, located towards the center of the heel of the foot 102 of the patient 100. When the patient 100 performs a toe off 120 in the stance phase, the body force of the patient has a toe off location of resultant force 122, as shown in FIG. 7B, located towards the center of the ball of the foot 102 of the patient 100. The swing phase 114 is the portion of the gait cycle when the foot 102 is off the ground. The swing phase 114 ends, along with the complete gait cycle 110, with the next heel strike 116' of the same foot 102. In swing phase 114, the foot 102 supports substantially no body force of the patient 100. In swing phase 114, foot 102 is not in contact with the ground surface 124 and therefore, foot 102 is supporting little, if any, of the body force of the patient 100.

2. The Foot Platform

The foot platform 10 of the preferred embodiments functions to move the foot 102 from an equilibrium position 18 to an activated position 20 by operating in the following modes: equilibrium mode and activated mode. The foot platform 10 is preferably in equilibrium mode when the foot platform 10 is supporting less than or equal to substantially half of the body force and, more preferably, is in equilibrium mode when the foot platform 10 is supporting less than or equal to approximately 65% of the body force. For example, the foot platform 10 is supporting less than or equal to substantially half of the body force in standing position. In equilibrium mode, the lateral segment 14 and the medial segment 16 of the foot platform 10 respond to the portion of the body force supported by the foot platform 10 such that the foot platform 10 allows the foot 102 to be positioned in an equilibrium position 18. In equilibrium position 18, as shown in FIGS. 3A, 4, and 5, the foot 102 is positioned such that the foot 102 is substantially parallel to a ground surface. The lateral side 104 of the foot is a first distance from the ground surface and the medial side 106 is a second distance from the ground surface. In equilibrium position 18, the first distance is preferably substantially equal to the second distance such that the foot 102 is positioned substantially parallel to the ground surface.

The foot platform 10 is in activated mode when the foot platform 10 is preferably supporting greater than substantially half of the body force and, more preferably, supporting greater than 65% of the body force and the location of the resultant force is preferably in the medial segment 16. For example, the foot platform 10 is supporting greater than substantially half of the body force in stance phase 112 such as during heel strike 116 or during tow off 120. In activated mode, the lateral segment 14 and the medial segment 16 respond to the portion of the body force supported by the foot platform such that the foot platform moves the foot to an activated position 20. In activated position 20, as shown in FIGS. 3B, 4, and 5, the foot 102 is positioned such that the foot 102 is at an angle to the ground surface. The lateral side 104 of the foot is a first distance from the ground surface and the medial side 106 is a second distance from the ground surface. In activated position 20, the first distance is preferably greater than the second distance such that the foot 102 is at an angle to the ground surface. This angle is known as an eversion angle of the foot 102, and is preferably increased in the activated position 20.

By the foot platform 10 moving the foot 102 from an equilibrium position 18 to an activated position 20, the adduction moment at the knee is reduced. As a result, the load between the medial compartment of the knee and the lateral compartment of the knee is preferably redistributed such that the ratio of the load in the medial compartment to the load in the lateral compartment is reduced. By reducing this ratio, the rate of cartilage deterioration in the medial compartment is therefore also preferably reduced along with preferably reducing the amount of pain experienced by the patient 100. Additionally, by the foot platform 10 moving the foot 102 from the equilibrium position 18 to the activated position 20, the transition of the foot 102 (as shown by arrow 22 in FIG. 1) between the equilibrium position 18 and the activated position 20 induces the upper body of the patient 100 to sway (as shown by arrow 108 in FIG. 1) such that the adduction moment at the knee is reduced. As a result, the load between the medial compartment of the knee and the lateral compartment of the knee is redistributed and the ratio of the load in the medial compartment to the load in the lateral compartment is reduced. The transition of the foot 102 (as shown by arrow 22 in FIG. 1) between equilibrium position 18 and activated position 20, preferably occurs substantially instantaneously once the foot platform 10 supports greater than substantially half of the body force, i.e. once the foot 102 enters stance phase 112. This change of the eversion angle of the foot 102 once the patient 100 steps with foot 102 induces the upper body of the patient 100 to sway (as shown by arrow 108 in FIG. 1) and the adduction moment at the knee is reduced. As a result, the load between the medial compartment of the knee and the lateral compartment of the knee is redistributed such that the ratio of the load in the medial compartment to the load in the lateral compartment is reduced, thereby preferably reducing the rate of cartilage deterioration in the medial compartment of the knee and preferably reducing the amount of pain experienced by the patient 100.

3. The Lateral Segment and the Medial Segment of the Foot Platform

Figure 8B:
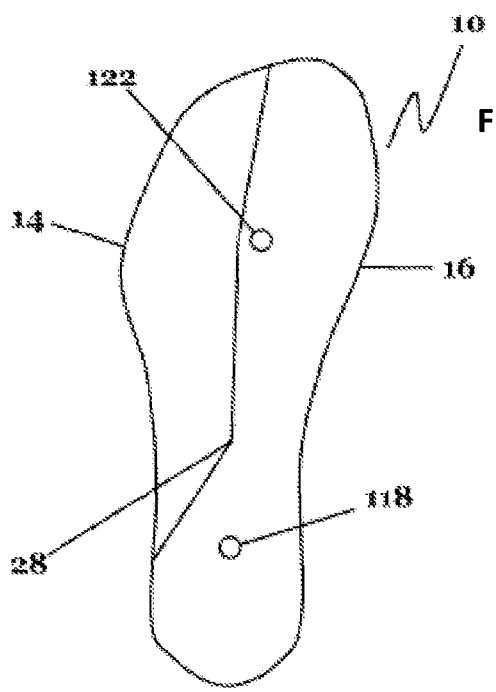
FIGS. 8A and 8B are drawings of variations of the transition line between the lateral segment and the medial segment.
Figure 8A:
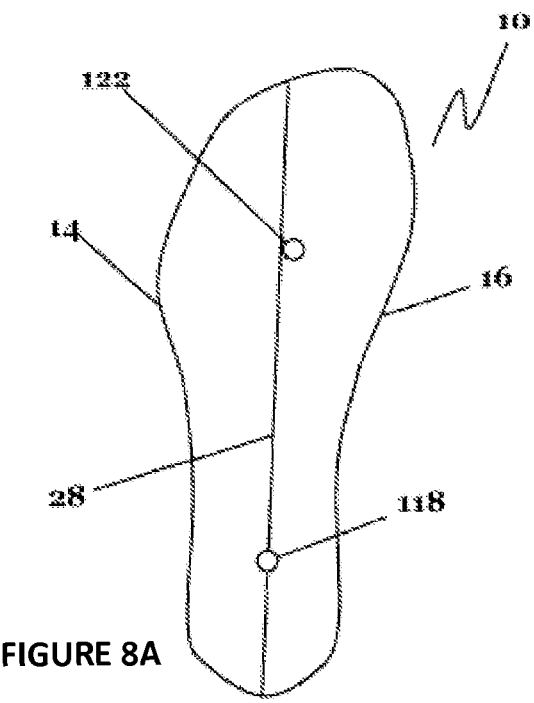

The lateral segment 14 and the medial segment 16 of the foot platform 10 of the preferred embodiments function to move the foot 102 from an equilibrium position 18 to an activated position 20 by responding to the portion of the body force supported by the foot platform 10. The lateral segment 14 and the medial segment 16 preferably have substantially the same thickness or height under the foot 102, such that in equilibrium position 18, the foot 102 is preferably substantially parallel to the ground surface. The lateral segment 14 and the medial segment 16 preferably run the length of the foot platform 10, or may alternatively be located in discrete portions of the foot platform as shown in FIG. 2. The transition line 28 between the lateral segment 14 and the medial segment 16 of the foot platform 10 is preferably designed such that it defines the geometry of the medial segment 16 of the foot platform 10 such that it supports both the heel strike location of resultant force 118 and the toe off location of resultant force 120, as shown in FIG. 8A. If the medial segment 16 and the lateral segment 14 had geometries exemplified in FIG. 8B, the medial segment 16 would not support both the heel strike location of resultant force 118 and the toe off location of resultant force 120. This would lead to a less than ideal response to the portion of the body force supported by the foot platform 10. Ideally, when the foot platform 10 is supporting greater than substantially half of the body force, for example, in stance phase 112 such as during heel strike 116 (where the foot platform 10 is supporting the heel strike location of resultant force 118) or during tow off 120 (where the foot platform 10 is supporting the toe off location of resultant force 122) the medial segment 16, as shown in FIG. 8A, will support the majority of the greater than substantially half of the body force and have a more efficient response to the portion of the body force supported by the foot platform 10 and therefore, more efficiently and effectively move the foot to an activated position 20.

The lateral segment 14 and the medial segment 16 of the foot platform 10 of the preferred embodiments preferably respond to the portion of the body force supported by the foot platform 10 in one of several variations. In a first variation, the lateral segment 14 has a lateral material stiffness 24 and the medial segment 16 has a medial material stiffness 26. In this variation, the lateral material stiffness 24 is preferably greater than the medial material stiffness 26. The lateral material stiffness 24 has preferably a 10% to 50% greater stiffness than the medial material stiffness 26, but may alternatively be any other suitable amount more stiff than the medial material stiffness 26. As shown in FIGS. 2 and 4, the cross sections of the lateral segment 14 and the medial segment 16 are preferably wedge, slide, or stepped shaped and preferably overlap. The cross sections of the lateral segment 14 and the medial segment 16 may alternatively overlap in any other suitable fashion. The cross sections of the lateral segment 14 and the medial segment 16 may alternatively, as shown in FIGS. 3A and 3B, not overlap and may but up vertically against one another.

As shown in FIGS. 3A, 3B, and 4, the lateral segment 14 and the medial segment 16 of the foot platform 10 move the foot 102 from an equilibrium position 18 to an activated position 20 by compressing in response to the portion of the body force supported by the foot platform 10. In equilibrium mode, the lateral segment 14 and the medial segment 16 preferably compress substantially the same amount such that the foot platform 10 allows the foot 102 to be positioned in an equilibrium position 18, as shown in FIGS. 3A and 4. In activated mode, the medial segment 16 compresses more than the lateral segment 14 such that the foot platform 10 moves the foot 102 to an activated position 20, as shown in FIGS. 3B and 4.

In a second variation, as shown in FIG. 5, the lateral segment 14 and the medial segment 16 of the foot platform 10 move the foot 102 from an equilibrium position 18 to an activated position 20 by moving from a first position to a second position in response to the portion of the body force supported by the foot platform 10. As shown in FIG. 5, the cross sections of the lateral segment 14 and the medial segment 16 are preferably wedge, slide, or stepped shaped and preferably overlap. The cross sections of the lateral segment 14 and the medial segment 16 may alternatively overlap in any other suitable fashion such that the medial segment 16 may slide, rock, or bend away from the lateral segment 14. The cross sections of the lateral segment 14 and the medial segment 16 may alternatively not overlap and may but up vertically against one another. In equilibrium mode, the lateral segment and the medial segment respond to the portion of the body force supported by the foot platform such that the lateral segment and the medial segment are in a first position relative to one another such that the foot platform 10 allows the foot 102 to be positioned in an equilibrium position 18, as shown in FIG. 5. In activated mode, the lateral segment and the medial segment respond to the portion of the body force supported by the foot platform such the lateral segment and the medial segment are in a second position relative to one another such that the foot platform 10 moves the foot 102 to an activated position 20, as shown in FIG. 5. To move from the first position to a second position, the medial segment preferably slides away from the lateral segment, but may alternatively bend, rock, or move away from the lateral segment in any other suitable fashion such that the foot platform 10 moves the foot 102 to an activated position 20, as shown in FIG. 5.

4. Therapeutic System for a Series of Patients

The therapeutic system and method of the preferred embodiments is preferably additionally designed for a series of patients and, more specifically, for a series of patients each having a body force, a foot having a lateral side and a medial side, and a knee having a medial compartment and a lateral compartment. The series of patients preferably includes as least a first patient having a first body force and a foot having a first foot size and a second patient having a second body force and a foot having a second foot size. The patients of the series of patients preferably all have the same foot size, while they may have different body forces (due to height or build). In a example, the first body force is greater than the second body force, while the first foot size is equal to the second foot size. The therapeutic system therefore includes a series of foot platforms all with the same size to fit the same foot sizes but with different lateral and medial segments, such that the foot platform is "tuned" to the body force of each patient. In a first variation, the first lateral segment has a first lateral material stiffness and the first medial segment has a first medial material stiffness, while the second lateral segment has a second lateral material stiffness and the second medial segment has a second medial material stiffness. Because the first body force is greater than the second body force, the first medial material stiffness is greater than the second medial material stiffness such that when the first foot platform is supporting greater than substantially half of the first body force, the first medial segment compresses the correct therapeutic amount for the first patient (i.e. more than the first lateral segment) and such that when the second foot platform is supporting greater than substantially half of the second body force, the second medial segment compresses the correct therapeutic amount for the second patient (i.e. more than the second lateral segment). In another example, the therapeutic system may be roughly "tuned" into two or three categories with particular thresholds between the categories (such as patients under 150 lbs, patients between 150 lbs and 210 lbs, and patients over 210 lbs).

The series of foot platforms "tuned" for the series of patients may include gender specific foot platforms, age specific foot platforms, cartilage deterioration level specific foot platforms, magnitude of knee adduction moment specific foot platforms, or any other suitable patient characteristic specific foot platforms each offered in a series of sizes to fit the range of foot sizes. Additionally, a patient may tune their foot platform on a daily or other characteristic dependent basis, such as cartilage deterioration or knee adduction moment magnitude.

Although omitted for conciseness, the preferred embodiments include every combination and permutation of the various foot platforms, the various lateral segments, the various medial segments, and the various series of foot platforms.

As a person skilled in the art will recognize from the previous detailed description and from the figures and claims, modifications and changes can be made to the preferred embodiments of the invention without departing from the scope of this invention defined in the following claims.

We claim:

1. A therapeutic system for a patient, comprising:
 a foot platform having
    a rear portion for supporting a heel of a foot of the patient,
    a front portion for support a front part of the foot of the patient, the front portion having a lateral segment and a medial segment;
 wherein the lateral segment has a first stiffness, the medial segment has a second stiffness, and the first stiffness is greater than the second stiffness;
 wherein the lateral segment with the first stiffness comprises a first material that extends to the rear portion, and the medial segment with the second stiffness comprises a second material that extends to the rear portion; and
 wherein a support surface of the foot platform formed at least in part by the medial segment is tiltable about an axis defined by the front and rear portions in response to a force imposed on the foot platform.

2. The therapeutic system of claim 1, wherein:
 the support surface has a tilted configuration about the axis when the force imposed on the foot platform exceeds a threshold; and the support surface has a configuration that is less tilted relative to the tilted configuration when the force imposed on the foot platform is equal to or below the threshold.

3. The therapeutic system of claim 1, wherein the first stiffness is at least 10% greater than the second stiffness.

4. The therapeutic system of claim 1, wherein the medial segment abuts against the lateral segment.

5. The therapeutic system of claim 4, wherein the medial segment is secured to the lateral segment.

6. A therapeutic system for a patient, comprising:
a foot platform having
   a rear portion for supporting a heel of a foot of the patient, the rear portion having a lateral segment and a medial segment,
   a front portion for support a front part of the foot of the patient;
wherein a support surface of the foot platform is formed at least in part by the medial segment;
wherein the lateral segment of the rear portion has a first stiffness, the medial segment of the rear portion has a second stiffness, and the first stiffness is greater than the second stiffness;
wherein the lateral segment of the rear portion comprises a first material, the medial segment of the rear portion comprises a second material; and
wherein the first material at the lateral segment of the rear portion extends to the front portion.

7. The therapeutic system of claim 6, wherein:
the support surface has a tilted configuration when a force imposed on the foot platform exceeds a threshold;
the support surface has a configuration that is less tilted relative to the tilted configuration when the force imposed on the foot platform is equal to or below the threshold.

8. The therapeutic system of claim 6, wherein the support surface is tiltable to lower a first side at the medial segment relative to a second side at the lateral segment.

9. The therapeutic system of claim 6, wherein the medial segment abuts against the lateral segment.

10. The therapeutic system of claim 9, wherein the medial segment is secured to the lateral segment.

11. The therapeutic system of claim 6, wherein the support surface of the foot platform is tiltable about an axis defined by the front portion and the rear portion in response to a force imposed on the foot platform.

12. The therapeutic system of claim 6, wherein the first stiffness is at least 10% greater than the second stiffness.

13. A therapeutic system for a patient, comprising:
a foot platform having
   a rear portion for supporting a heel of a foot of the patient, the rear portion having a lateral segment and a medial segment,
   a front portion for support a front part of the foot of the patient;
wherein a support surface of the foot platform is formed at least in part by the medial segment;
wherein the lateral segment of the rear portion has a first stiffness, the medial segment of the rear portion has a second stiffness, and the first stiffness is greater than the second stiffness;
wherein the lateral segment of the rear portion comprises a first material, the medial segment of the rear portion comprises a second material; and
wherein the medial segment is not fixedly secured to the lateral segment so that the medial segment can slide or rock away from the lateral segment.

14. A therapeutic system for a patient, comprising:
a foot platform having
   a rear portion for supporting a heel of a foot of the patient, the rear portion having a lateral segment and a medial segment,
   a front portion for support a front part of the foot of the patient;
wherein a support surface of the foot platform is formed at least in part by the medial segment;
wherein the lateral segment of the rear portion has a first stiffness, the medial segment of the rear portion has a second stiffness, and the first stiffness is greater than the second stiffness;
wherein the lateral segment of the rear portion comprises a first material, the medial segment of the rear portion comprises a second material; and
wherein the second material at the medial segment of the rear portion extends to the front portion.

15. A therapeutic system, comprising:
a foot platform having
   a rear portion for supporting a heel of a foot of the patient, the rear portion having a lateral segment and a medial segment,
   a front portion for support a front part of the foot of the patient, the front portion having a lateral segment and a medial segment;
wherein the lateral segment of the rear portion comprises a first material, the medial segment of the rear portion comprises a second material, and the first material at the lateral segment of the rear portion is stiffer than the second material at the medial segment of the rear portion; and
wherein the lateral segment of the front portion comprises the first material.

16. The therapeutic system of claim 15, wherein:
a support surface of the foot platform has a tilted configuration when a force imposed on the foot platform exceeds a threshold; and
the support surface has a configuration that is less tilted relative to the tilted configuration when the force imposed on the foot platform is equal to or below the threshold.

17. The therapeutic system of claim 15, wherein the lateral segment of the rear portion has a first stiffness, the medial segment of the rear portion has a second stiffness, and the first stiffness is at least 10% greater than the second stiffness.

18. The therapeutic system of claim 15, wherein a support surface of the foot platform is tiltable to lower a first side at the medial segment relative to a second side at the lateral segment.

19. The therapeutic system of claim 15, wherein the medial segment abuts against the lateral segment.

20. The therapeutic system of claim 19, wherein the medial segment is secured to the lateral segment.

21. The therapeutic system of claim 15, wherein a support surface of the foot platform is tiltable about an axis defined by the front portion and the rear portion in response to a force imposed on the foot platform.

22. A therapeutic system, comprising:
a foot platform having
   a rear portion for supporting a heel of a foot of the patient, the rear portion having a lateral segment and a medial segment,
   a front portion for support a front part of the foot of the patient, the front portion having a lateral segment and a medial segment;

wherein the lateral segment of the rear portion comprises a first material, the medial segment of the rear portion comprises a second material, and the first material at the lateral segment of the rear portion is stiffer than the second material at the medial segment of the rear portion; and wherein the lateral segment of the front portion is stiffer than the medial segment of the front portion.

* * * * *

UNITED STATES PATENT AND TRADEMARK OFFICE
CERTIFICATE OF CORRECTION

PATENT NO. : 8,387,277 B2  
APPLICATION NO. : 12/144569  
DATED : March 5, 2013  
INVENTOR(S) : Thomas Andriacchi et al.

Page 1 of 1

It is certified that error appears in the above-identified patent and that said Letters Patent is hereby corrected as shown below:

In the specification

Replace column 1, lines 7-10:
"This invention was supported in part by grant number AR049792 from National Institute of Health (NIH) and Department of Veterans Affairs grant number A3476R The US. Government has certain rights in the invention."

with

--This invention was made with Government support under contract AR049792 awarded by the National Institutes of Health. The Government has certain rights in the invention.--

Signed and Sealed this  
Tenth Day of November, 2015

Michelle K. Lee  
*Director of the United States Patent and Trademark Office*